US007344027B2

United States Patent
Erickson et al.

(10) Patent No.: US 7,344,027 B2
(45) Date of Patent: Mar. 18, 2008

(54) SHARPS CONTAINER FOR "NO-TOUCH," SEQUENTIAL SAFE STORAGE OF USED PEN NEEDLES

(75) Inventors: Thomas E. Erickson, Crosslake, MN (US); James J. Erickson, Mound, MN (US); Timothy A. Bachman, Saint Paul, MN (US)

(73) Assignee: Ultimed, Inc., St. Paul, MN (US)

( * ) Notice: Subject to any disclaimer, the term of this patent is extended or adjusted under 35 U.S.C. 154(b) by 605 days.

(21) Appl. No.: 10/862,835

(22) Filed: Jun. 7, 2004

(65) Prior Publication Data

US 2005/0269226 A1 Dec. 8, 2005

(51) Int. Cl.
B65D 83/10 (2006.01)
(52) U.S. Cl. .................... 206/366; 206/370
(58) Field of Classification Search ............. 206/363, 206/366, 370; 221/36, 37, 40, 45, 101; 604/192, 604/263
See application file for complete search history.

(56) References Cited

U.S. PATENT DOCUMENTS

| 4,862,573 | A | * | 9/1989 | Kelson et al. ............. 29/240 |
| 5,409,113 | A | | 4/1995 | Richardson et al. |
| 5,469,964 | A | * | 11/1995 | Bailey ..................... 206/364 |
| 5,494,158 | A | | 2/1996 | Erickson |
| 5,545,145 | A | | 8/1996 | Clinton et al. |
| 5,573,113 | A | | 11/1996 | Shillington et al. |
| 5,918,739 | A | * | 7/1999 | Bilof et al. ............... 206/366 |
| 5,971,966 | A | | 10/1999 | Lav |
| 6,685,017 | B2 | | 2/2004 | Erickson |
| 6,923,318 | B1 | * | 8/2005 | Erickson et al. ........... 206/366 |
| 6,923,319 | B1 | * | 8/2005 | Erickson et al. ........... 206/366 |
| 2003/0040715 | A1 | | 2/2003 | D'Antonio et al. |
| 2003/0132129 | A1 | | 7/2003 | Erickson |

FOREIGN PATENT DOCUMENTS

DE  35 06218 A1  2/1985
GB  2 376 892 A  12/2002

* cited by examiner

*Primary Examiner*—David T. Fidei
(74) *Attorney, Agent, or Firm*—Crompton, Seager & Tufte LLC

(57) ABSTRACT

A sharps container for safe storage of used pen needles comprises a housing within which is rotatably mounted a used pen needle receiving and ejecting means. Used pen needles are inserted into the receiving means. The receiving and ejecting means is rotated; during the rotation, cam follower means connected to the ejecting means engages cam means within the housing to cause the ejection of the used pen needle into the housing.

13 Claims, 4 Drawing Sheets

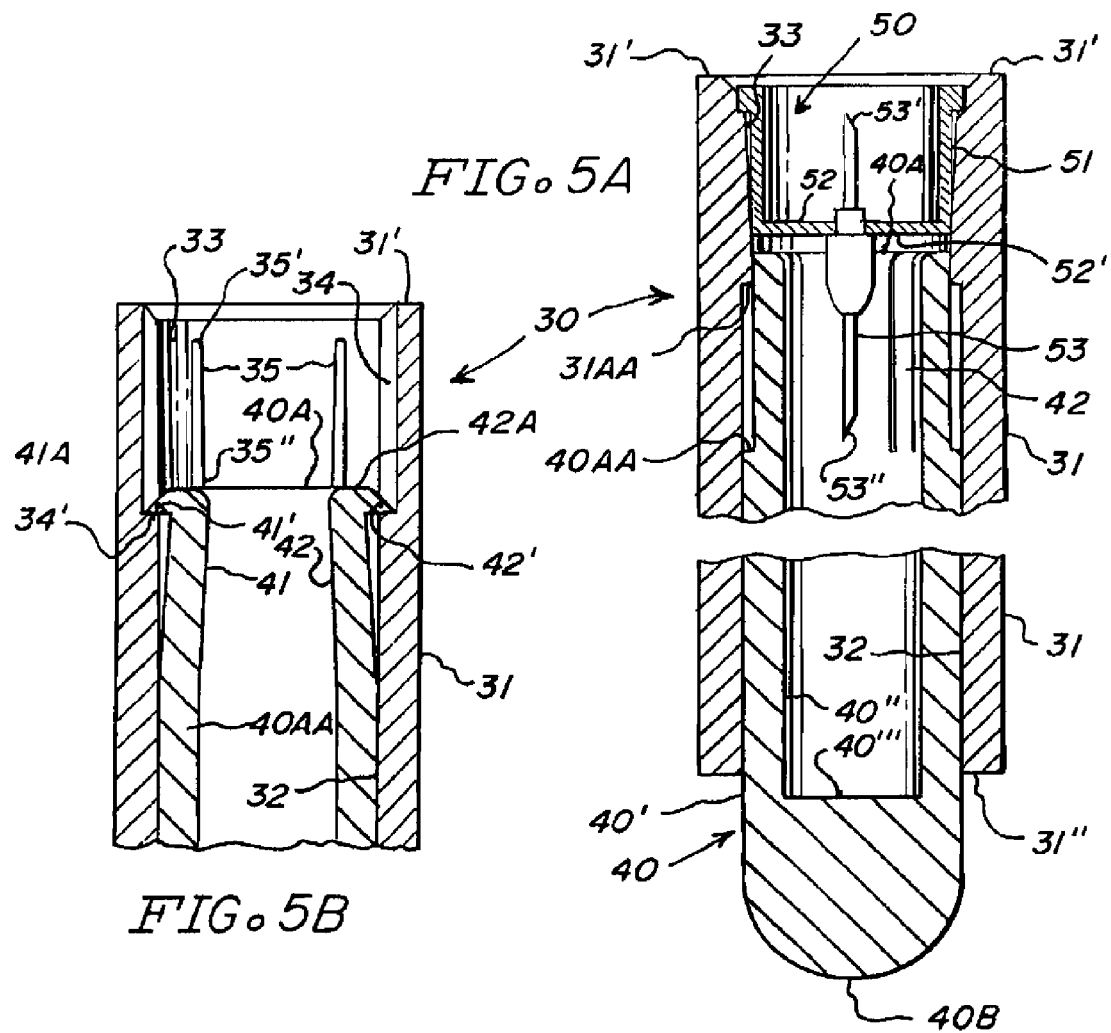
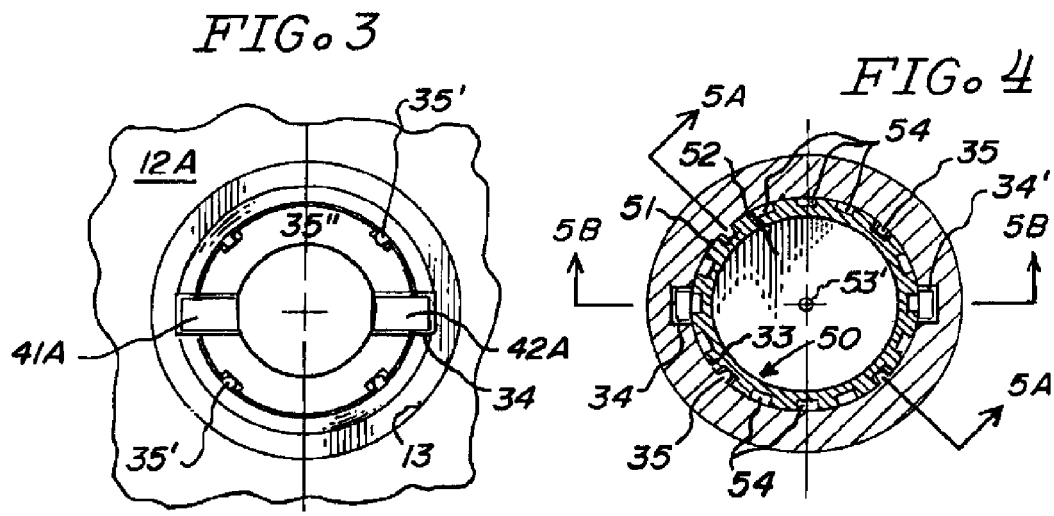

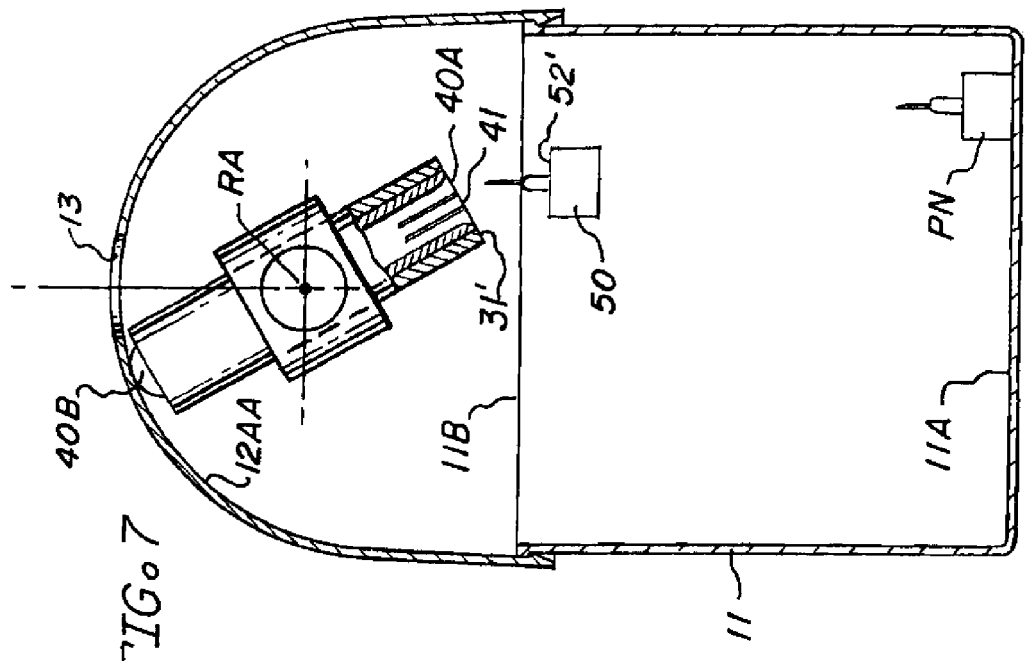
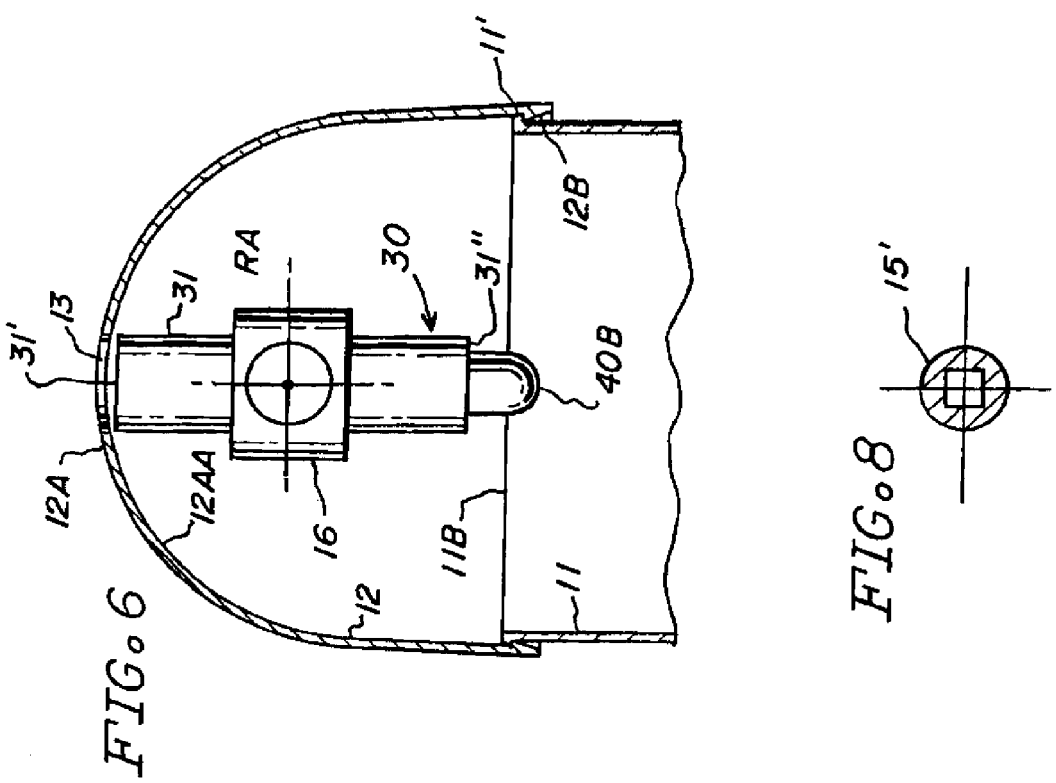
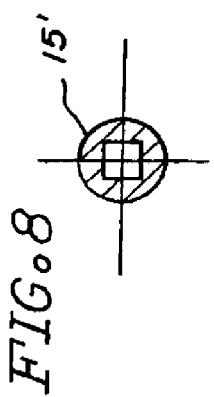

SHARPS CONTAINER FOR "NO-TOUCH," SEQUENTIAL SAFE STORAGE OF USED PEN NEEDLES

BACKGROUND AND FIELD OF THE INVENTION

This invention relates generally to a "sharps" container for used pen needles (sometimes hereafter referred to as "PNs") and specifically to a sharps container for used PNs which provides the safe (no-touch) sequential feeding or insertion of used PNs into the container for safe storage therein.

Because of well known health issues, the safe disposal of syringes and other "sharps" has long been a high priority for medical related professional facilities and industries. Prior art sharps containers are found in public venues such as hospitals, medical clinics, and retail establishments. These containers are usually securely attached to some base means and have a lock means to permit controlled and safe removal of used "sharps."

There are also prior art "portable" sharps containers for syringes, examples being U.S. Pat. No. 5,494,158 and 6,685,017 showing sharps containers which necessarily are large because of the size of the elongated syringes.

Medical delivery pens (hereinafter sometimes "MDPs") have, more recently, become widely used instead of or in addition to syringes, e.g., by diabetics, who frequently inject themselves several times a day with accurately measured, adjustable, pre-selected amounts of insulin or other medication. Medical delivery pens include a reservoir of medication and a distal end adapted to be attached (usually by thread means) to a pen needle assembly (PNA). As is well known (see, for example FIG. 1 of U.S. Pat. No. 5,545,145), the pen needle assembly has (within an outer, generally cylindrical shield 28) a generally cylindrical housing 26 within which is mounted an axially extending hollow needle 21, (i) the proximal end 24 of which punctures a seal in the distal end 16 of the medical delivery pen 10 (to allow the flow there-through of medication) when the delivery pen is screwed into the proximal end of the pen needle cylindrical housing 26, and (ii) the distal end 22 of which is for insertion into tissue of the person requiring the medication. The pen needle assemblies typically include a removable thin sterile seal covering the proximal (large diameter) end of the said outer shield and a removable tube-like shield covering the distal portion of the hollow needle. The assembled pen needle assembly is then factory sterilized. The user of a pen needle assembly removes the seal from the outer shield, screws the pen into the proximal end of the pen needle housing, removes the outer and tube-like shields, sets the medical delivery pen for the desired dose of medication, and then inserts the distal end of the pen needle into the target tissue following which the medical delivery pen is actuated to deliver the desired dose of medication through the hollow needle into said tissue.

Many diabetics routinely administer medication to themselves several times a day by injection of a pre-selected quantity of insulin (or substitute medication) in liquid form; the correct amount of medication can be determined from prior professional medical instruction or by use of convenient portable blood analysis kits which are small, compact and provide rapid indicators of the user's blood sugar level. The several daily injections are often done away from the diabetic's home or residence which has made the use of the portable, convenient medical delivery pens widespread. The aforesaid testing kits and the medical delivery pens are relatively small in size and can easily fit within a woman's purse or equivalent. A typical scenario for a diabetic at a meal is to first use the blood sugar testing kit to obtain an indicator of his or her blood sugar level. This information then facilitates programming or adjusting the medical delivery pen to deliver the desired quantity of medication. Then the pen with an attached PN (a PNA sans the outer protective shield) is used to inject the medication. These steps require a relatively short length of time and can be done with minimum loss of privacy.

MDPs are also widely used by doctors, nurses and other professionals in their duties. Many individuals will request (sometimes insist) that an injection be done with a pen needle rather than a syringe. The aforementioned professionals are especially mindful of possible dangers from a needle stick and the possible unwanted "sticks" that occur in the professional world.

In a perfect world, the user (both individual and professional) of a pen needle assembly would, after the first use of a pen needle, carefully detach the used PN from the medical delivery pen and safely dispose said PN. The approved disposal procedure is (i) insertion of the distal end of the needle into the tube-like shield (sometimes omitted) and thence the shielded needle and PN cylindrical housing into the outer shield, (ii) unscrewing of the medical delivery pen from the proximal end of the pen needle cylindrical housing, and (iii) careful placement of the used pen needle assembly into a safe sharps container. Alas, the recommended procedure is not always followed. Used (and potentially dangerous) PNs or PNAs are routinely left in unsafe places where third parties may unwittingly be "stuck." Examples of such unsafe places are purses, the pockets on the back of aircraft seats, private and public wastebaskets, garbage cans, dumpsters and empty milk or other unsafe containers.

Further, the above described disposal procedure requires that the user (or associate) handle or hold the PN while the pen is unscrewed therefrom; this creates the possibility of a potentially dangerous stick Also, if the user (or associate) tries to insert the PN into the outer shield to form a PNA, then additional handling is again required with the possibility of a "stick"

One prior art example of a container for unused and used pen needle assemblies is U.S. Pat. No. 5,545,145 which shows a tube containing a small number of unused pen needle assemblies arranged in axial alignment. This patent also teaches that, as unused assemblies are removed from one end of the tube, then a used assembly may be inserted into the tube from the other end. The tube is adapted to be attached to the side of a medical delivery pen. This arrangement has significant shortcomings. The capacity is quite limited and, potentially dangerous "sticks" could occur when a user (or associate) tries to insert a used PN (with or without the protective outer shield) into the used end of the tube.

The present invention provides a totally "no-touch" means for a user of a PNA to transfer a used PN from a pen into the unique used PN sharps container for safe storage therein without, as indicated, any touching of the used PN by the user.

SUMMARY OF THE INVENTION

This invention provides a sharps container for safe manual, sequential "feeding" of used PNs into the container for safe storage therein. The container is a housing with an internal storage space sized to hold a plurality of used PNs. A used PN receiving and ejecting means is provided within the housing and includes (i) manually rotatable means connected to the housing for rotation about an axis, (ii) an ejector assembly connected to the manually rotatable means (to rotate therewith about the axis) and including a cam follower means, and (iii) cam means on the housing positioned to contact and actuate the cam follower means upon rotation of the manually rotatable means, the "actuation" of the cam follower means causing the "ejection" of the PN into the container.

The invention provides a sharps container which is especially useful for an individual such as a diabetic who may require several daily doses of medication, which doses are required throughout the day (frequently at meal time) and thus may occur at the users residence but are often at other locations such as the user's place of work, at a restaurant, in an automobile or aircraft, etc. The container can be relatively compact and sized to fit within a woman's purse or equivalent.

BRIEF DESCRIPTION OF THE DRAWINGS

FIG. 3 is an enlarged view of that part of the top 12A of the housing that includes a port or opening 13 as shown in FIG. 2 and as viewed along section lines 3-3 thereof.

FIG. 4 is an enlarged view of the ejector means 30 shown in FIG. 2 as viewed along section lines 4-4 thereof and including a pen needle 50 positioned in the ejector means 30.

FIG. 5A is a cross-section view of the ejector means 30 as viewed along section lines 5A-5A of FIG. 4, this view showing the pen needle 50.

FIG. 5B is a cross-section view of the ejector means 30 as viewed along section lines 5B-5B of FIG. 4 but with the pen needle 50 removed to enable the showing of ribs 35 of the ejector means 30.

FIGS. 6 and 7 are somewhat schematic views of the housing and the ejector means showing the ejector means in two orientations when rotated about the axis by the manually rotatable means.

FIG. 8 is a cross-section view of the rotatable means as viewed along section lines 8-8 of FIG. 2.

DETAILED DESCRIPTION OF THE INVENTION

Figure 1:
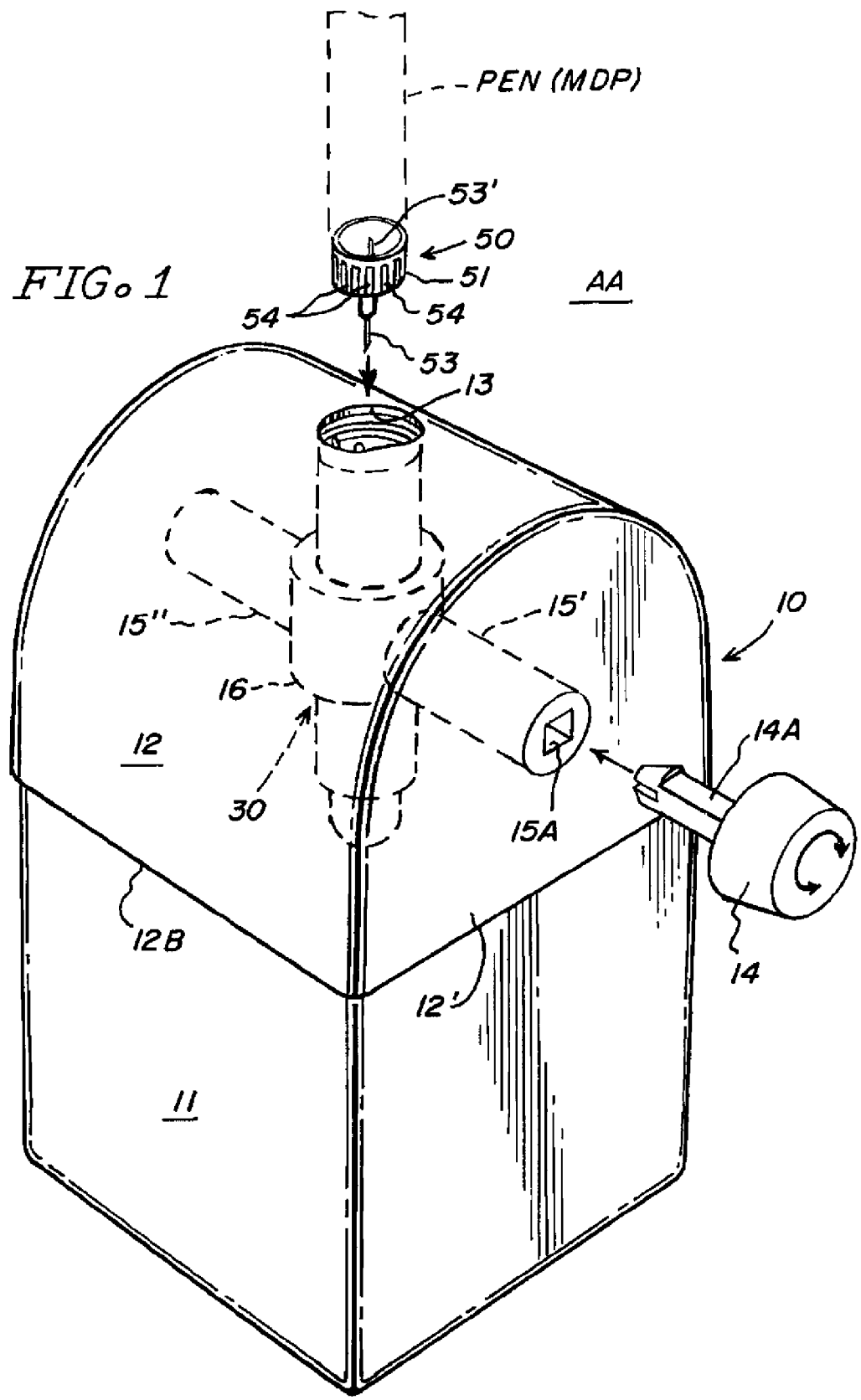
FIG. 1 is a top, side isometric view of the preferred embodiment of a PN sharps container provided by the invention.
Figure 2:
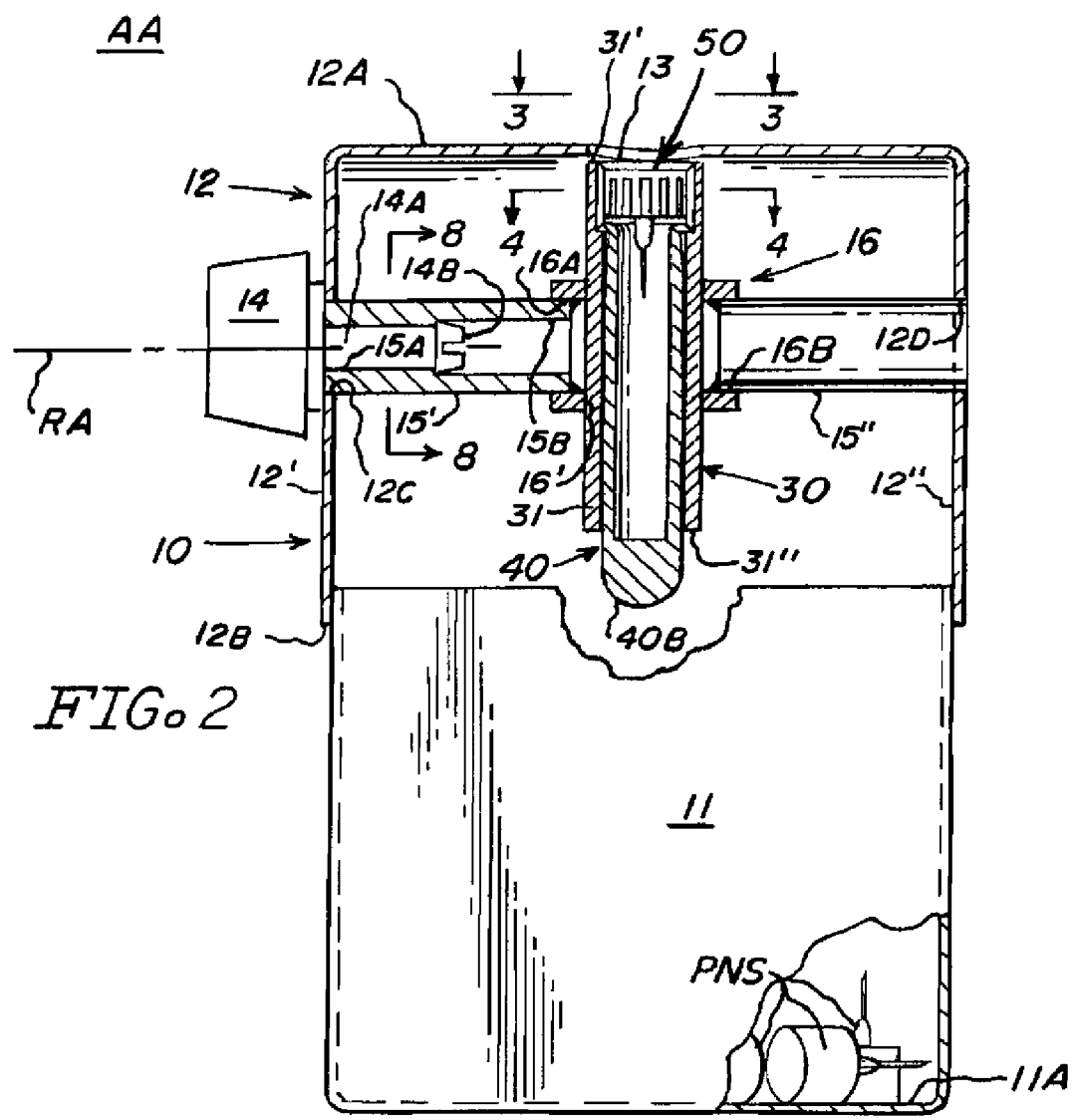
FIG. 2 is a side view, partly in section, of the container of FIG. 1.

In FIG. 1 a sharps container AA provides a means for the safe, i.e., "no direct human touching" storage of used pen needles. The container AA comprises a housing 10 having a bottom or storage section 11 and an upper or cover section 12 which fit together as is shown clearly in FIGS. 2, 6 and 7 to define an internal storage space sized to facilitate the safe storage of a plurality of used pen needles. Thus section 11 has sides and a bottom surface 11A for receiving the used pen needles and a top edge 11B with a rim 11'. Cover section 12, as viewed in FIGS. 6 and 7 has a curved shape about an axis. The top 12A of the cover section 12 has an opening 13 sized to permit the axial insertion therethrough of a used pen needle PN also identified in the drawings by reference numeral 50. The bottom edge 12B of the cover section 12 has an inwardly extending latch portion which co-acts with rim 11' to provide a locking means for sections 11 and 12. Section 12 has two planar ends 12' and 12" shown best in FIG. 2.

FIG. 1 shows, in phantom, a medical delivery pen (MDP) of the well known types currently used having at the distal end thereof male thread means for attachment to female threads in the proximal end of a pen needle 50. It should be understood that pen needle 50 shown in FIG. 1 has already been used and the user desires to safely remove the used pen needle from the pen and thence place the used pen needle into safe storage means. The pen needle 50 has a cylindrical surface 51 with a pre-selected outer diameter. The cylindrical surface 51 also has a plurality of longitudinally extending shallow grooves 54 (see FIGS. 1, 2 and 4) which co-act with ribs 35 of the pen needle receiving and ejecting assembly 30, described below, to hold the pen needle against rotation about its longitudinal axis when the user unscrews the pen therefrom.

A manually rotatable means comprising an external knob 14 with connected shafts 15' and 15" and a central collar 16 rotatably supported by bearing means 12C and 12D in ends 12' and 12" respectively of the housing for rotation, relative to the housing, about a rotational axis RA. The collar 16 has a central bore sized to receive and firmly hold the ejector assembly 30 and additionally has means 16A and 16B for attachment thereto of the inboard ends of shafts 15' and 15". Shaft 15' has a bore ISA with a square cross-section for receiving a square cross-section shaft 14A connected to external knob 14. Thus rotation of the knob 14 will rotate the ejector assembly 30 about the rotational axis RA.

The ejector assembly 30, for this embodiment, is shown to comprise an elongated tubular member 31 having two ends, an upper end 31' and a lower end 31". The upper end 31' per se is best shown in FIG. 5B and comprises a bore 33 sized to receive the aforesaid pre-selected outer cylindrical surface 51 of used pen needle 50. Bore 33 axially extends from end 31' a pre-selected distance terminating with an inwardly extending shoulder means 34'. A plurality of axially extending ribs 35 are integral with tubular member 31 and extend radially inward from the sides of the bore 33 a sufficient amount so as to engage the shallow grooves 54 of the pen needle 50 to provide the above described holding function.

The remaining bore of tubular member 31 is identified by reference numeral 32; thus bores 32 and 33 together have a pre-selected axial length, the two ends of which are defined by the ends 31' and 31" of the tubular member 31. Importantly, the ends 31' and 31" are approximately equidistant from the rotational axis RA. Further, the total axial length of the tubular member 31 is pre-selected, regard being given to the size of the housing 10, so that it may be rotated about the rotational axis RA without contacting the inside surface 12AA of the housing but yet have the end 31' (for the used pen needle receiving function) adjacent to opening 13 of the housing.

An elongated ejector means 40 has a pre-selected axial length and a cylindrical shape 40' sized to snuggly, but slidably fit within bores 32 and 33 (for relative axial movement therewith) is shown in FIGS. 2, 5A, 5B, 6 and 7. At the top of a first end 40A (as shown in FIG. 5A) of the ejector means 40, a longitudinally extending bore 40''' is provided which extends to an end surface 40''' which is adjacent to the bottom or second end 40B. End 40B is curved to provide a cam follower surface. It is important to note that end 40B normally extends a pre-selected distance beyond the end 31" of tubular member 31; this is shown in FIG. 5A.

The ejector means 40 includes an integral pair of latch arms 41 and 42 having, respectively, latch means 41' and 42' for engagement with shoulder means 34'; this provides a holding function to prevent the ejector means 40 from being moved axially out of the tubular member 31 (downward as shown in FIG. 5A). However, as described below, the entire ejector means 40 is, during the used pen needle ejection phase, moved upwardly (as shown in FIG. 5A) by the camming action of cam follower 40B contacting the cam surface 12AA on the inside of housing 10. FIG. 7 shows the ejector means 40 at its maximum axial displacement relative to the tubular member 31. Such upward, axial motion of the ejector means relative to the member 31, while sufficient to eject the used pen needle, is limited by a stop means 40AA (on ejector means 40) abutting against an internal shoulder 31AA of member 31.

FIG. 5A shows the used pen needle 50 positioned in the recessed bore 33 with the cylindrical surface 51 and associated grooves 54 in firm engagement with bore 33 and its associated ribs 35. Referring to FIG. 5B, it is seen that the ribs 35 are slightly tapered from top 35' to bottom 35"; this taper function of ribs 35 in combination with reverse tapers of the grooves 54 on the cylindrical surface 51 of the used pen needle facilitates the aforesaid firm holding of the pen needle. To explain further, when the pen user inserts the pen needle 50 through the opening 13 of the housing and thence into the recessed bore 33, there will be enough axially force applied by the user via the pen to the pen needle to firmly engage the pen needle to the member 31 following which the user will unscrew the pen from the pen needle. FIG. 5A also shows the radial wall 52 of the pen needle, and the centrally positioned, axially extending hollow needle 53 having a proximal end 53' and a distal end 53". The bore 40" is axially sized to accommodate all expected lengths of needles.

Referring to FIG. 6, it is seen that the used pen needle receiving and ejecting means 30 is oriented about the rotational axis RA so that the end 31' is adjacent to and aligned with the opening 13 of the housing 12. It should be understood, for this explanation, that a used pen needle is already positioned within bore 33 as aforesaid. In this view, the cam follower 40B is shown extending out end 31' of tubular member 31. To eject the pen needle, the knob 14 is manually rotated clockwise as shown in FIG. 6; this rotation continues to the orientation shown in FIG. 7. Beginning prior to this point the cam follower 40B has had initial contact with the inside curved surface 12AA of the housing. As the clockwise rotation continues the cam follower (and the entire ejector means 40) is subject to an axial force tending to move the ejector means 40 in the axial direction toward end 31'. The end result is that the used pen needle 50 will be ejected out of the bore 33 into the bottom of the housing as is shown in FIG. 7. Note in FIG. 7 that the end 40A of the ejector 40 is co-planar with end 31' of tubular member 31. The magnitude of the axial force applied to the used pen needle 50 during the ejection is a function of the level of co-action between the ribs 35 and grooves 54; the force can vary to impart a range of velocities to the ejected pen needle. In all cases, the invention provides for the safe storage of the used pen needles; the ejection velocity of the used pen needle being irrelevant because they are confined within the housing.

The apparatus is then available to safely dispose of additional used pen needle assemblies. The user rotates the knob 14 to an angular position as shown in FIGS. 1 and 6 whereat the next used pen needle (on the end of a pen) may be inserted, via opening 13, into the bore 33.

It will be understood that the pen user does not have to touch the used pen needle either to (i) remove the used pen needle from the pen, or (ii) dispose the used pen needle into a safe storage means.

While we have shown our preferred embodiment of the invention, it will be understood that variations may be made without departing from the inventive concept. For example, while the ejector mechanism has been positioned within a tubular member, other means may provide the elongated bore means within which the ejector mechanism is positioned. Accordingly, the invention is to be limited only by the scope of the following claims.

The invention claimed is:

1. A sharps container for facilitating the safe manual, sequential feeding of cylindrically shaped used pen needles into said container for safe storage therein, said pen needles having a pre-selected outer diameter, and said container comprising:
  A. housing means with an internal storage space sized to facilitate the safe storage therein of a plurality of used pen needles, and
  B. used pen needle receiving and ejecting means within said housing means and including:
    (1) manually rotatable means connected to said housing means for rotation relative to said housing means about an axis,
    (2) a pen needle ejector assembly having an ejector axis and connected to said rotatable means to be rotated thereby about said axis, said ejector assembly comprising (i) an elongated means having recessed means at a first end thereof sized to receive a used pen needle and (ii) an ejector member connected to said elongated member for relative axial movement therewith and having (a) cam follower means at one end thereof initially positioned a pre-selected axial distance along said ejector axis beyond a second end of said elongated means, and (b) a second end initially positioned adjacent said used pen receiving means, and
    (3) cam means connected to and within said housing positioned for contacting said cam follower means when said rotatable member and said ejector assembly is rotated about said axis to thereby move said ejector member axially with respect to said elongated means toward said first end thereof so that a second end of said ejector member provides a pen needle ejecting motion;
  whereby, when a pen needle is positioned in said recessed means and said manually rotatable means is rotated about said axis sufficiently so that said cam follower means contacts said cam means, said ejector member will force said pen needle axially out of said recessed means into said container storage space.

2. The sharps container of claim 1 wherein said elongated means comprises a tube means of pre-selected axial length having first and second ends and an internal bore within which is positioned said ejector member.

3. The sharps container of claim 1 further including an opening in said housing sized to admit the axial insertion of a used pen needle therethrough.

4. The sharps container of claim 3 wherein said ejector assembly is selectively oriented about said axis by rotation of said manual rotatable means between (i) an initial position with said recessed means being adjacent to and in alignment with said opening to facilitate the axial insertion of an used pen needle into said recessed means, and (ii) a second position whereat said cam follower means engages said cam means, following which additional rotation of said ejector assembly about said axis causes the ejection of a used pen needle from said recessed means into said housing for safe storage therein.

5. A sharps container for facilitating the safe manual, sequential feeding of cylindrically shaped used pen needles into said container for safe storage therein, said pen needles having a pre-selected outer diameter, and said container comprising:
  A. housing means with an internal storage space sized to facilitate the safe storage therein of a plurality of used pen needles; and
  B. used pen needle receiving and ejecting means within said housing means and including:
    (1) manually rotatable means connected to said housing means for rotation relative to said housing means about an axis,
    (2) an ejector assembly connected to said rotatable means to be rotated thereby about said axis, said ejector assembly comprising a member having (i) elongated bore means of pre-selected axial length and first and second ends, said first end of said bore means being sized to receive said pre-selected outer diameter of a pen needle, (ii) said bore means having shoulder means adjacent to said first end, and (iii) elongated ejector means positioned within said bore means with latch means at one end thereof for engagement with said shoulder means and with cam follower means at a second end thereof, said ejector means being axially sized so that said cam follower means extends beyond said second end of said bore means when said latch means is in engagement with said shoulder means, and
    (3) cam means connected to said housing and positioned for contacting said cam follower means when said rotatable member is rotated about said axis to thereby move said latch means of said ejector means axially away from said shoulder means toward said first end of said bore means to provide an ejecting motion;
  whereby, when a pen needle is positioned in said first end of said bore and said manually rotatable means and connected ejector means is rotated about said axis sufficiently so that said cam follower means contacts said cam means, said ejector means will force said pen needle axially out of said bore means into said container storage space.

6. The sharps container of claim 5 wherein said ejector assembly comprises a tube means of pre-selected axial length having first and second ends and an internal bore within which is movably positioned said ejector means.

7. The sharps container of claim 6 wherein said internal bore includes a shoulder adjacent to said first end of said tube means and the portion of said internal bore between said first end of said tube means and said shoulder means is sized to closely receive said pre-selected outer diameter of a pen needle.

8. The sharps container of claim 7 wherein said portion of said internal bore includes radially extending means for gripping said pre-selected outer diameter of a pen needle.

9. The sharps container of claim 5 including an opening in said housing sized to allow the axial insertion of a pen needle therethrough, and said used pen needle receiving and ejecting means being oriented with respect to said opening so that said first end of said bore means may be rotated into close proximity to said opening to facilitate the insertion of an used pen needle therein.

10. The sharps container of claim 5 wherein said cam means is integral with said housing.

11. The sharps container of claim 1 wherein said recessed means of said elongated member includes radially extending means.

12. The sharps container of claim 11 wherein said radially extending means comprises a plurality of longitudinally extending ribs.

13. The sharps container of claim 12 wherein said longitudinally extending ribs are longitudinally tapered to facilitate engagement with a used pen needle positioned in said recessed means.

* * * * *